(12) United States Patent
Harari et al.

(10) Patent No.: US 8,801,658 B2
(45) Date of Patent: Aug. 12, 2014

(54) BREASTFEEDING MILK CONSUMPTION MEASURING DEVICE

(75) Inventors: Tzach Harari, Givatayim (IL); Liat Huller-Harari, Givatayim (IL); Shaye Kivity, Ramat Gan (IL)

(73) Assignee: Innovia Medical Ltd, Givatayim (IL)

( * ) Notice: Subject to any disclaimer, the term of this patent is extended or adjusted under 35 U.S.C. 154(b) by 177 days.

(21) Appl. No.: 13/201,862

(22) PCT Filed: Feb. 17, 2010

(86) PCT No.: PCT/IL2010/000142
§ 371 (c)(1),
(2), (4) Date: Aug. 17, 2011

(87) PCT Pub. No.: WO2010/095133
PCT Pub. Date: Aug. 26, 2010

(65) Prior Publication Data
US 2012/0004603 A1 Jan. 5, 2012

Related U.S. Application Data

(60) Provisional application No. 61/152,977, filed on Feb. 17, 2009.

(51) Int. Cl.
*A61M 1/06* (2006.01)
(52) U.S. Cl.
USPC .......................................................... 604/74
(58) Field of Classification Search
USPC ...................................................... 604/74–46
See application file for complete search history.

(56) References Cited

U.S. PATENT DOCUMENTS

| 4,024,856 | A | 5/1977 | Kirianoff | |
|---|---|---|---|---|
| 4,338,953 | A | 7/1982 | Ward | |
| 4,924,862 | A | 5/1990 | Levinson | |
| 7,833,177 | B2 * | 11/2010 | Long et al. | 600/587 |
| 8,114,030 | B2 * | 2/2012 | Ales et al. | 600/584 |
| 2004/0044288 | A1 * | 3/2004 | Gorenberg et al. | 600/481 |
| 2008/0077042 | A1 * | 3/2008 | Feldkamp et al. | 600/547 |
| 2008/0097169 | A1 | 4/2008 | Long et al. | |
| 2010/0217148 | A1 * | 8/2010 | Binder | 600/547 |
| 2012/0277636 | A1 * | 11/2012 | Blondheim et al. | 600/595 |

OTHER PUBLICATIONS

Daly, S.J. et al; "The determination of short-term breast volume changes and the rate of synthesis of human milk using computerized breast measurement" Experimental Physiology (online), Jan. 1, 1992, vol. 77, No. 1, pp. 79-87 [retrieved on Jun. 22, 2010] Retrieved from the internet: <URL:http://ep.physoc.org/content/77/1/79.full.pdf>. Entire document especially pp. 80-83.

* cited by examiner

*Primary Examiner* — Aarti B Berdichevsky
(74) *Attorney, Agent, or Firm* — D. Gador

(57) ABSTRACT

A device and method for measuring an amount of breast milk suckled during a breastfeeding session, the device including a mechanism for determining the change in volume of a breast during the breastfeeding session (before breastfeeding and after breastfeeding), and a calculation unit for calculating therefrom the quantity of milk suckled during the breastfeeding session.

11 Claims, 10 Drawing Sheets

SECTION A-A

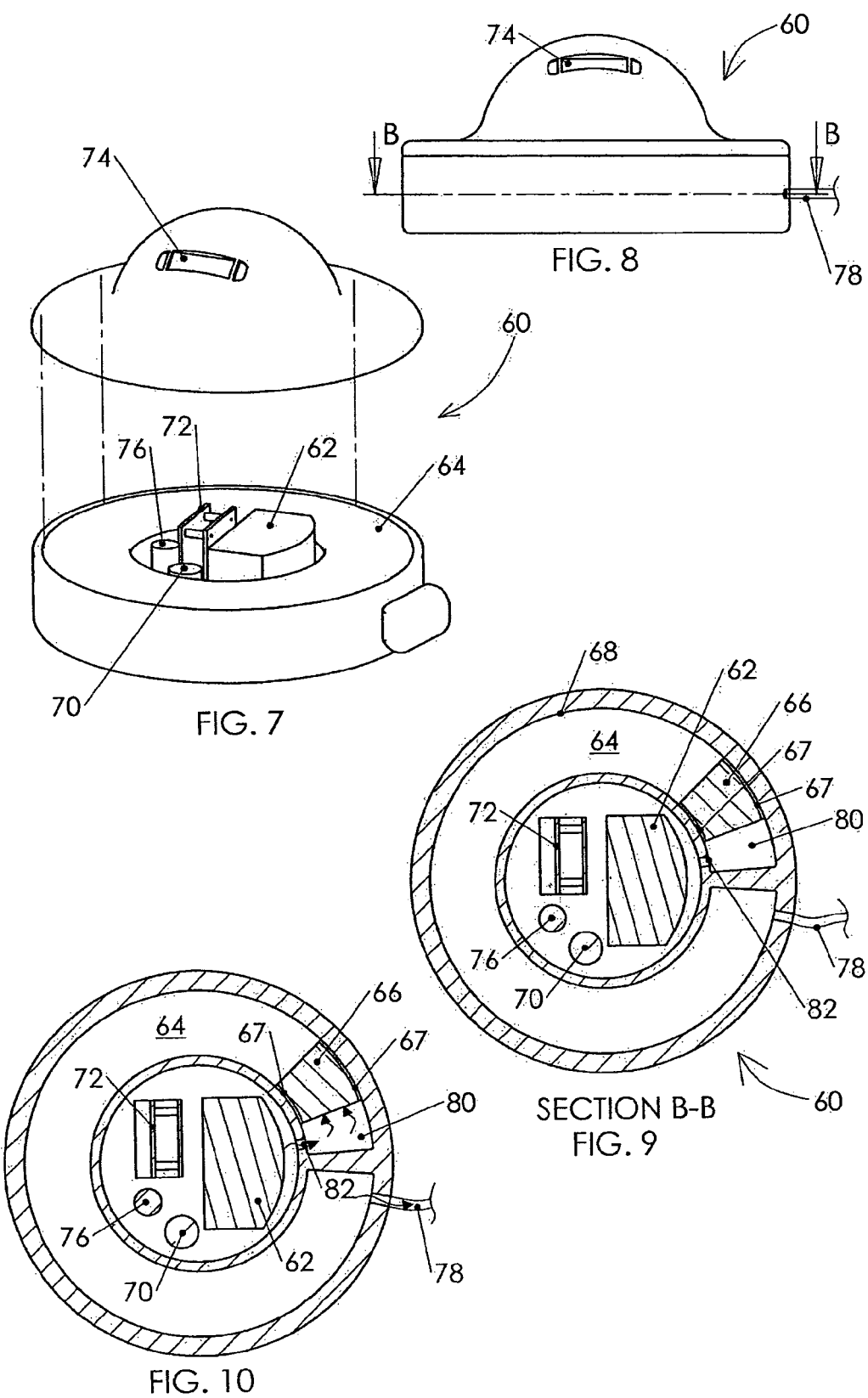

SECTION C-C

BREASTFEEDING MILK CONSUMPTION MEASURING DEVICE

FIELD OF THE INVENTION

The present invention relates to devices for measuring the quantity of breast milk, in general and, in particular, to a device for measuring the quantity of breast milk consumed during breastfeeding.

BACKGROUND OF THE INVENTION

The need to measure the amount of breast milk suckled by a baby is important to many lactating mothers. This information will help to evaluate the baby's nutritional status, the need for breastfeeding guidance, or the use of milk substitutes, and therefore is important to the pediatrician, as well. Although breastfeeding is very important for the baby's health, many mothers discontinue breastfeeding and start using formulas. The main reason for stopping breastfeeding is the mother's false impression and worry that insufficient milk is consumed by the baby.

A number of devices for measuring the amount of milk expressed during breastfeeding have been proposed. These devices generally tried to adopt methods of fluid flow measurement and typically include a flow or capacity measuring device. These measuring devices are mounted on the breast during breastfeeding and measure the amount of milk flowing therethrough. A few examples of such devices are shown in U.S. Pat. No. 5,827,191 to Rosenfeld and US Patent Application publication no. 2008/0039741 to Shemesh et al., US 2005/0177099 to Dahan. Other devices propose the use of flow gauges utilizing ultrasound measurements or piezoelectric devices. These proposals did not solve the problem for two reasons: first, because such flow gauges are of relatively low precision, particularly when attempting to measure relatively small and varying amounts of liquid. Second, the invasive nature of the flow measurement devices interferes with the intimate nature of the mother/baby feeding and bonding process.

Yet other proposals include weighing the mother and/or baby or measuring the fullness of the baby's stomach before and after nursing, for example, as shown in US Patent application 2008/0097169 to Long, et al., 2008/0077040 to Ales, et al. and 2008/0077042 to Feldkamp, et al. These proposals did not succeed either, because of the lack of precision (precision of milliliters is required) and because of the inconvenience involved.

Accordingly, there is a long felt need for an accurate method of measuring the quantity of breast milk suckled by a baby, and it would be very desirable if such a method were non-invasive and did not interfere with the nursing process.

SUMMARY OF THE INVENTION

The present invention provides an answer to the need for measuring the volume of milk consumed as a baby breastfeeds. This innovative apparatus measures the breastfeeding quantity in a non-direct method, which does not interfere with the intimate mother-baby connection during breastfeeding. The invention measures changes in the breast volume during breastfeeding. The difference between breast volume before and after breastfeeding is proportional to the amount of milk transferred to the baby, particularly during the first weeks after birth. Thus, the proposed apparatus provides a solution by enabling the mother to measure the quantity of breast milk without interfering with the mother-newborn bonding.

There is provided according to the present invention a device for measuring an amount of breast milk suckled during a breastfeeding session, the device including a mechanism for determining the change in volume of a breast during the breastfeeding session (before breastfeeding and after breastfeeding), and a calculation unit for calculating therefrom the quantity of milk suckled during the breastfeeding session.

According to one embodiment, the mechanism for determining the change in volume includes a mechanism for measuring the quantity of fluid in a space around the breast, and the calculation unit is coupled to the mechanism for measuring for receiving said measured quantity and calculating said quantity of milk from a change in said measured quantity of fluid before and after the breastfeeding session.

According to one embodiment, the mechanism for determining change includes a breast interface for placing on a breast, the breast interface defining an expandable space, a fluid pump for introducing fluid into the space, a fluid pressure gauge coupled to the space and to the fluid pump for measuring fluid pressure in the space for indicating a initial point and a end point for introduction of fluid to the space by the fluid pump, and a device for providing an indication of a total volume of fluid introduced to the space.

According to a preferred embodiment of the invention, the breast interface includes a rigid envelope and an elastic membrane affixed to the rigid envelope, and the space is defined between the rigid envelope and the elastic membrane.

According to some embodiments, the mechanism for determining a change includes a fluid chamber coupled to the space forming a closed system, a piston sealingly mounted in the chamber for slideable movement therethrough, a fluid pumping mechanism coupled to a driving chamber for introducing and removing fluid to the driving chamber for driving the piston through the fluid chamber, and a position encoder for indicating a position of the piston.

According to some embodiments, the device is coupled to a computing device. According to some embodiments, the device is coupled to a device Internet server.

There is further provided, according to the invention, a method for measuring an amount of breast milk expressed during a breastfeeding session, the method including determining a change of volume of the breast during breastfeeding (i.e., from before the breastfeeding session to after the breastfeeding session) and calculating therefrom the quantity of milk suckled from the breast.

According to one embodiment of the invention, the step of determining includes providing a breast interface for placing on a breast, the breast interface defining an internal space, coupling a fluid pump to the breast interference for introducing fluid into or removing fluid from the space, coupling a stop mechanism to the fluid pump for stopping the pump, and providing an indication of a quantity of fluid pumped into the space until the pump was stopped.

Further according to one embodiment, the step of determining includes placing a breast interface defining an internal space on the breast before the breastfeeding session, introducing fluid into the space until a predefined pressure is reached, placing the breast interface on the breast after the breastfeeding session, introducing fluid into the space until the predefined pressure is reached, calculating a change in quantity of fluid introduced into the space until the predefined pressure was reached before breastfeeding and after breastfeeding, and calculating from the change in quantity the quantity of milk consumed during the breastfeeding session.

According to some embodiments of the invention the method further includes providing a calculation unit for performing said calculations, providing an electronic board in the calculation unit, the electronic board including a connection interface for connection to a computing device, providing a connection interface on the electronic board, uploading breastfeeding data from the memory chip to a data file in the computing device, coupling the computing device to a device Internet server, uploading the breastfeeding data from the data file to the device Internet server, and analyzing the breastfeeding data in the device Internet server.

BRIEF DESCRIPTION OF THE DRAWINGS

The present invention will be further understood and appreciated from the following detailed description taken in conjunction with the drawings in which:

FIG. 7 is a partially exploded view of a unit for calculating milk quantity, according to one embodiment of the invention;

FIG. 8 is a front view of the device of FIG. 7;

FIG. 9 is a sectional view of the device of FIG. 8, taken along line B-B;

FIG. 10 is an enlarged view of FIG. 9 illustrating the fluid flow therethrough;

DETAILED DESCRIPTION OF THE INVENTION

The present invention relates to a device and method for measuring the quantity of breast milk a baby suckles during a breastfeeding session. The device measures changes in the breast volume during breastfeeding, which are proportional to the amount of milk transferred to the baby. An accurate and unique device and method to measure changes in the breast volume is described in the following paragraphs. During the measuring process, the breast is fully covered with a device cup, while the device measures the space between the cup and the breast. Changes in this space's volume reflect changes in the breast's volume. According to these changes, the amount of milk transferred to the baby is calculated.

The quantity of milk is calculated using a new method of indirectly measuring the volume of a breast by implementing an initialization process and introducing into or removing fluid from a space of defined volume around the breast until a fixed reference value is reached, e.g., using a pressure gauge, and calculating the change in the measured volume before and after the breastfeeding session.

Figure 1:
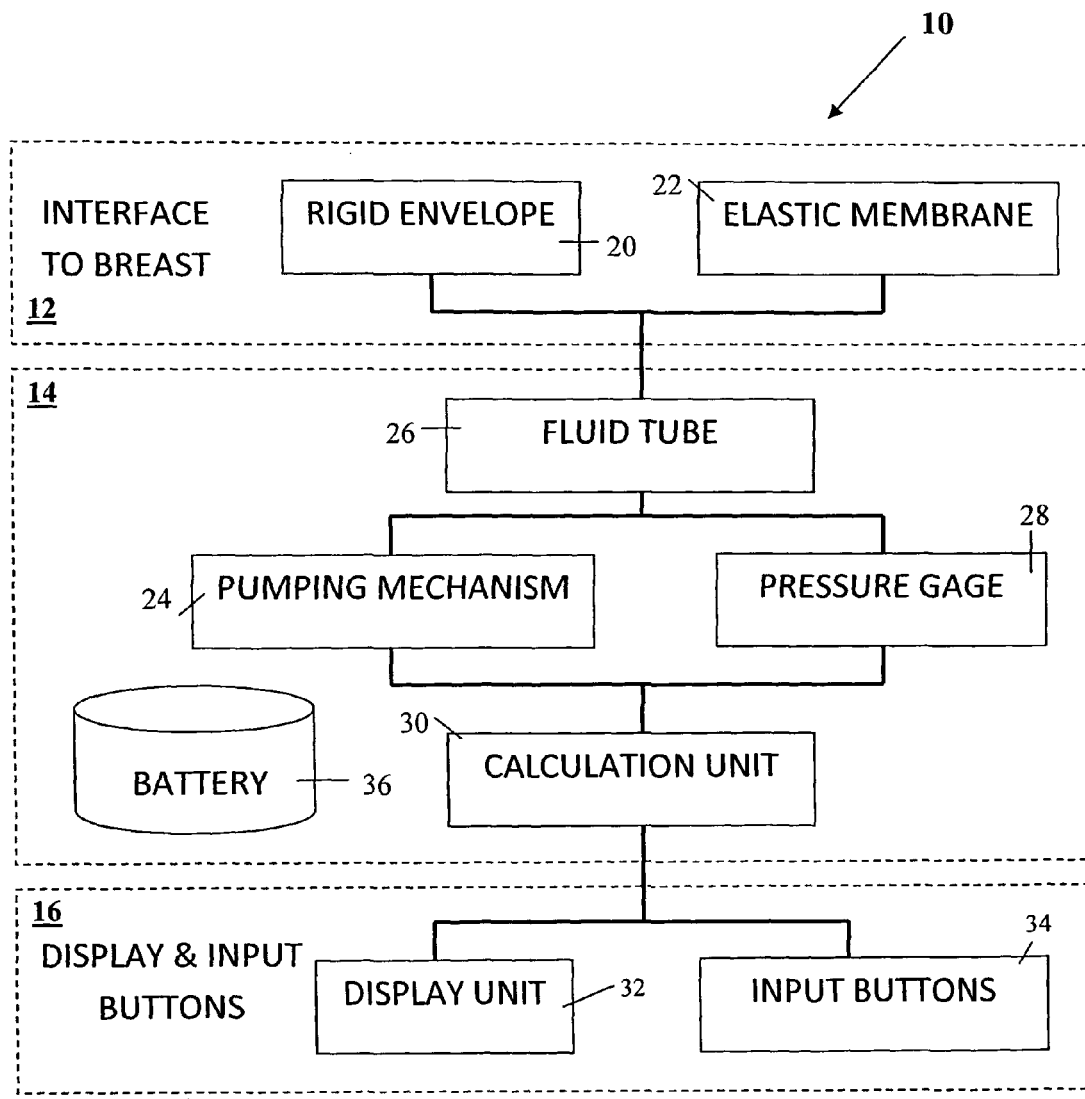
FIG. 1 is a block diagram illustration of a device for measuring a quantity of breast milk, according to the present invention.
Figure 2:
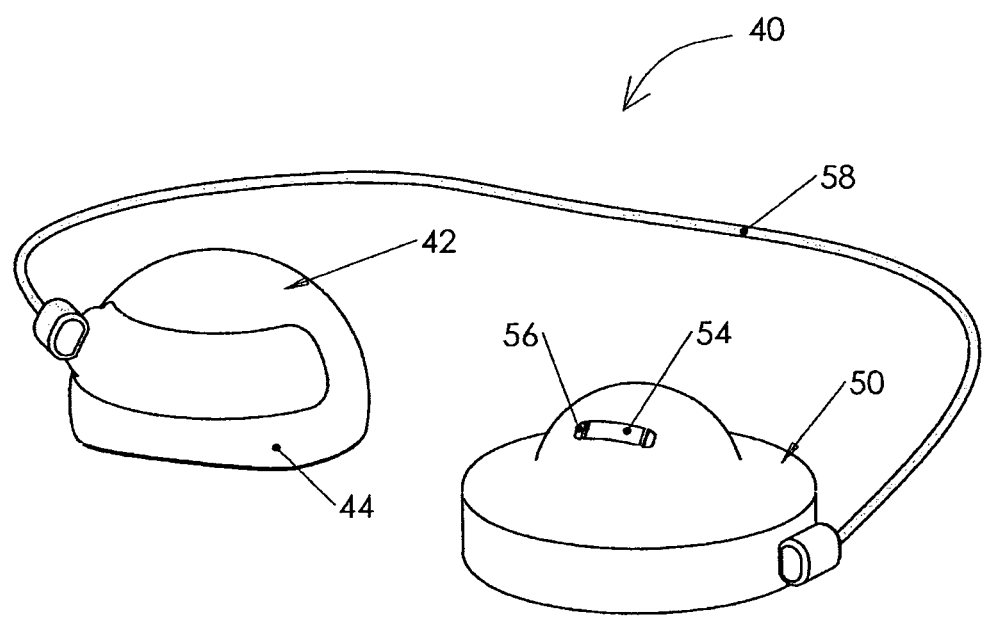
FIG. 2 is a schematic perspective illustration of a device for measuring a quantity of breast milk, constructed and operative in accordance with one embodiment of the present invention.
Figure 3:
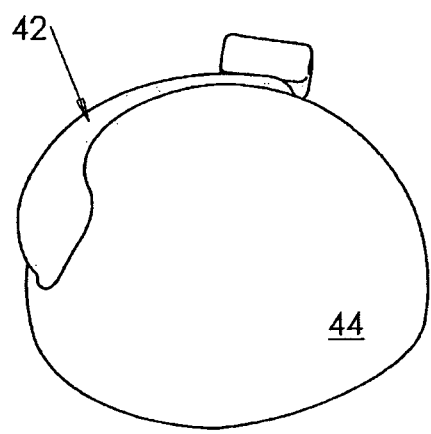
FIGS. 3, 4 and 5 are schematic side, top perspective and bottom perspective illustrations of a portion of the device of FIG. 2.
Figure 4:
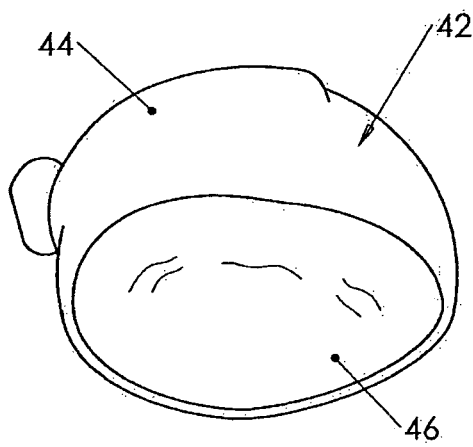
Figure 5:
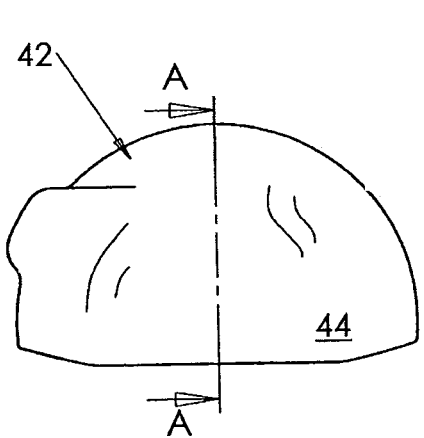
Figure 6:
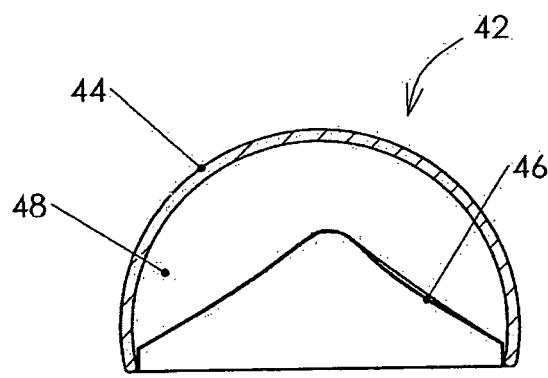
FIG. 6 is a sectional view of the portion of FIG. 5, taken along line A-A.
Figure 11A:
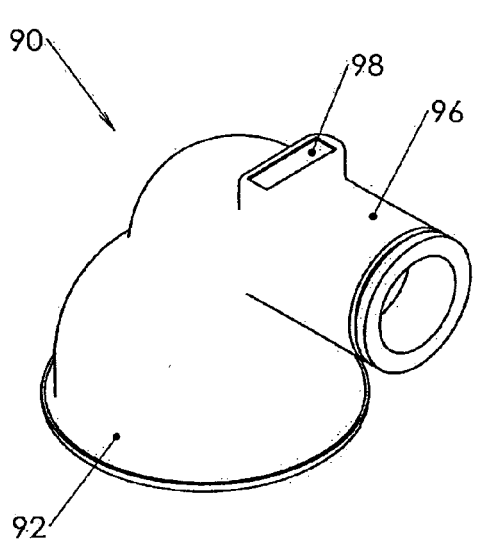
FIGS. 11a to 11d are schematic top perspective, bottom perspective, side and sectional illustrations, respectively, of a device for measuring a quantity of breast milk, constructed and operative in accordance with an alternative embodiment of the present invention.
Figure 11B:
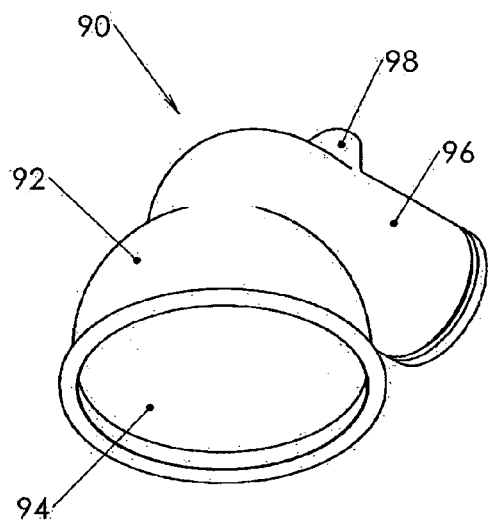
Figure 11C:
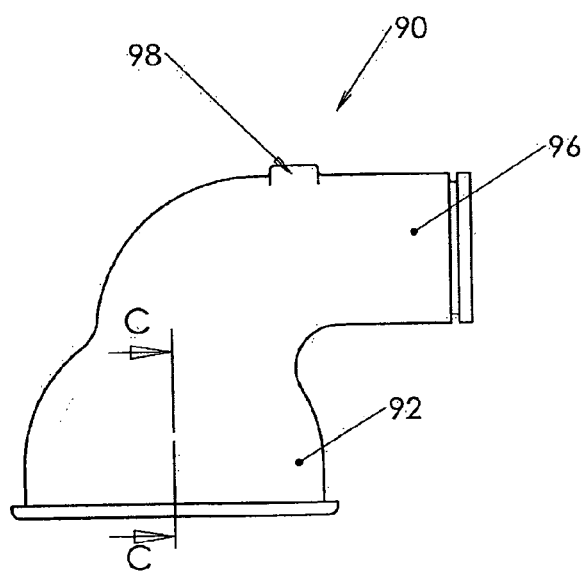
Figure 11D:
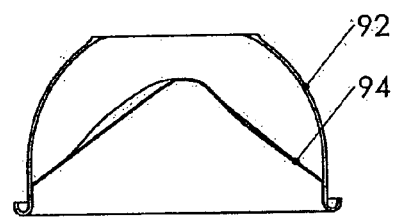

Referring now to FIG. 1, there is shown a block diagram illustration of a device 10 for measuring a quantity of breast milk, according to the present invention. Device 10 includes an interface 12 to a breast, a unit 14 for calculating milk volume and a user interface 16. Breast interface 12 includes a rigid envelope 20 lined with an elastic membrane 22. Elastic membrane 22 is formed of a suitably flexible, biocompatible material that can be placed on and conform to the shape of a breast.

Preferably, the shape and the material of the elastic sheet membrane will be designed and defined to enable the following properties:

Sufficient elasticity of the sheet membrane to enable working in the elastic range of the material at a rated pressure. The mechanical properties of the sheet membrane substantially do not change with use during the lifetime of the device. The sheet membrane returns to its original shape when the load (i.e., fluid pressure) is removed. Under normal use, the membrane will not reach the plastic range of the material and will not tear apart.

The mechanical properties of the sheet membrane enable working at a pre-determined constant pressure for different breast shapes. This pre-determined pressure value is selected so as to distribute the force evenly along the sheet membrane, permitting it to follow the breast shape geometry at the selected pressure.

The mechanical properties of the sheet membrane permit it to be securely attached to other parts of the device, without sealing problems.

Examples of materials that enable such properties can be found in the Silicone materials group, and latex.

The elastic membrane sheet can be seamed or seamless to enable it to conform to the rigid cup shape in the initial condition and to reach the breast shape during measurement, as described in detail below. According to another embodiment, the mechanical properties of the sheet or other breast engaging portion permit it to conform to the breast shape in the first stage and return to the initial position in a second stage, as by evacuating fluid from the device.

It is a particular feature of these embodiments of the invention that an internal space of variable volume is defined between rigid envelope 20 and elastic membrane 22 that can be filled with a fluid, such as air. This space permits indirect measurement of the volume of the breast and, thus, the quantity of milk suckled by the baby.

Unit 14 for calculating milk quantity includes a fluid pumping mechanism 24 for pumping pressurized fluid through a fluid tube 26 to and from the space between spherical envelope 20 and elastic membrane 22. A stop mechanism, here illustrated as a pressure gauge 28, is provided, coupled to pumping mechanism 24 and fluid tube 26, for sensing a rise in pressure and sending a cut-off signal to pumping mechanism 24 when a pre-defined pressure is reached. Unit 14 also includes a calculation unit 30, such as micro-controller, coupled to the pumping mechanism 24, pressure gauge 28 and user interface unit 16, for calculating breast volume before and after breastfeeding and calculating therefrom the quantity of breast milk suckled by the baby. a mechanism for indicating a quantity of fluid pumped into said space until said pump was stopped.

Preferably, a power source, such as a battery 36, is provided for powering all the electronic components of device 10.

User interface 16 includes a display 32 and a keyboard or input buttons 34. Display 32 can be designed and programmed to merely display the calculated quantity of breast milk, or may be a more complex display indicating time, date, breast volume before and after, etc., in addition to the calculated quantity of breast milk. A plurality of input buttons 34 are provided for a user to input control data or other information, as desired. As a minimum, buttons 34 are provided to indicate when measurement before breastfeeding should start and when measurement after breastfeeding should start. If it is desired to input compensation factors to the calculations, such as the age of the baby, etc., such data can also be input via buttons 34 or other optional input unit of the device. Alternatively, instead of a visual display and input buttons, a microphone and speakers can be provided for audio introduction and display of data.

FIGS. 2 to 6 are schematic illustrations of a device 40 for measuring a quantity of breast milk, constructed and operative in accordance with one embodiment of the present invention. There are two main components to device 40, which may be manufactured from appropriate polymers by injection molding. The first component is a breast interface unit 42 formed of a rigid spherical envelope 44 with a thin elastic sheet membrane 46 inside and affixed thereto (best seen in FIGS. 4 and 6). A space 48 is defined between spherical envelope 44 and membrane 46. A fluid, such as air or liquid, can be introduced into and removed from space 48, causing membrane 46 to change its shape, accordingly. Breast interface unit 42 is placed to fully cover the breast, with the unit's edge touching the chest.

The second component is a unit 50 for measuring breast volume change and calculating milk quantity. Unit 50 includes a pumping mechanism, a calculation unit and a control system, all not shown, and a user interface, including a display unit 54 and a keyboard or buttons 56. These two main components are connected by a fluid tube 58 that pushes fluid by means of the pumping mechanism to the space 48 between the rigid envelope 44 and the elastic membrane 46. The evacuation of the fluid from that space is preferably accomplished by the same pumping mechanism through the same fluid tube. Preferably, fluid tube 58 delivers the fluid to the space via several points (not shown) to ensure that all the space is filled with fluid. The rigid envelope shape may contain an inner fluid manifold that enables fluid inlet via several points.

The pumping mechanism can fill and evacuate air or other fluid to/from the space 48 between the rigid envelope 44 and the elastic membrane 46. As described in detail hereinbelow, the device measures the quantity of fluid that is pumped in, before and after breastfeeding, and calculates the difference.

According to this embodiment, the rigid envelope 44 is similar to a half sphere shell. Its design is friendly to the mother's body and the breast interface unit 42 does not contain any electric components. The shape of the device is designed to best fit the breast geometry. The unique curvature of the dome edge is designed to follow the mother's chest, to fully cover the breast and to enable accurate repetitive positioning of the device.

The elastic sheet membrane 46 is made of a thin elastic polymer. The thin elastic polymer shape and properties enable inflating different liquid volume sizes, at a pre-determined nominal pressure. The membrane 46 is compliant enough to conform to the shape of the envelope at a first stage and to conform to the shape of the breast at the second stage at a pre-selected pressure value, which is the pressure at which the volume measurement is made. The membrane 46 is attached to the rigid envelope 44 along the device edge that faces the breast. Preferably, several sizes of the breast interface will be provided to fit different breast sizes, for example, according to brassiere sizes.

Referring now to FIGS. 7 to 9, there are shown partially exploded, plan and sectional views of a unit 60 for calculating milk quantity, constructed and operative in accordance with one embodiment of the invention. Unit 60 includes a pumping mechanism, here illustrated as an air blower 62, arranged to blow air into an annular air chamber 64. A mechanism is also provided for indicating the quantity of fluid pumped into (or removed from) the space from the time the pump mechanism began pumping until the pump was stopped, In this embodiment, this mechanism is a position encoder 68, here illustrated as an electronic position encoder, is provided to measure the angle/distance a piston 66 moves through air chamber 64 as air is blown into a driving chamber 80. Piston 66 is arranged for sealing engagement with the inner walls of the air chamber 64, as by means of sealing pads 67. A pressure gauge 70 is provided in unit 60 to measure the air pressure in chamber 64 and in the void in the breast interface, and provide a cut-off signal to air blower 62 when the air pressure in chamber 64 reaches the pre-selected value, as described below. An electronic circuit board 72, or other control element, is provided in unit 60 to control the blower and encoder, and includes a micro-controller or other calculation module for calculating the air volume introduced into the driving chamber, the change in volume of the breast, and the quantity of milk indicated thereby. Electronic board 72 is drivingly coupled to a display 74. During the breastfeeding milk measuring process, the micro-controller receives input data from the pressure gage and pumping mechanism encoder, in order to compute the amount of milk delivered to the baby, and writes it to the memory. The micro-controller receives input data from the memory, and sends the result as output data to the display component. Preferably, a power source, such as a battery 76, is also provided in unit 60 to power all the electric and electronic components. An air tube 78 is coupled at one end to air chamber 64 and, at the other end (not shown), to the breast interface.

It will be appreciated that, alternatively, a linear fluid chamber can be utilized.

FIG. 10 is an enlarged view of unit 60 illustrating the fluid flow therethrough. Air chamber 64 is coupled to the expandable space between the shell and the elastic liner membrane in the breast interface and, preferably, is a closed system. As can be seen, air blower 62 blows air into driving chamber 80 via an air inlet 82. As driving chamber 80 fills with air, it pushes piston 66 along air chamber 64, forcing the air therein out through air tube 78 to the void between the cup and the elastomer. When the elastomer substantially conforms to the breast, the air pressure in the chamber increases dramatically. When this pressure increase is sensed by pressure gauge 70, the gauge sends a signal to the control unit in the electric board, which sends a signal to air blower 62 to stop blowing. The quantity of air moved from air chamber 64 to breast interface void is measured, as by means of the position encoder 68, and recorded in the control unit on board 72. It will be appreciated that blower 62 can operate in reverse, sucking the air from the void in the breast interface back into air chamber 64 until the elastomer sheet in the breast interface conforms to the inner shape of the rigid cup.

FIGS. 11a to 11d are schematic illustrations of a device 90 for measuring a quantity of breast milk, constructed and operative in accordance with an alternative embodiment of the present invention. In this embodiment, device 90 includes the breast interface 92 with elastomer liner 94, fluid blower and milk calculation unit 96 and user interface 98, as described above, in a single unit.

Figure 12:
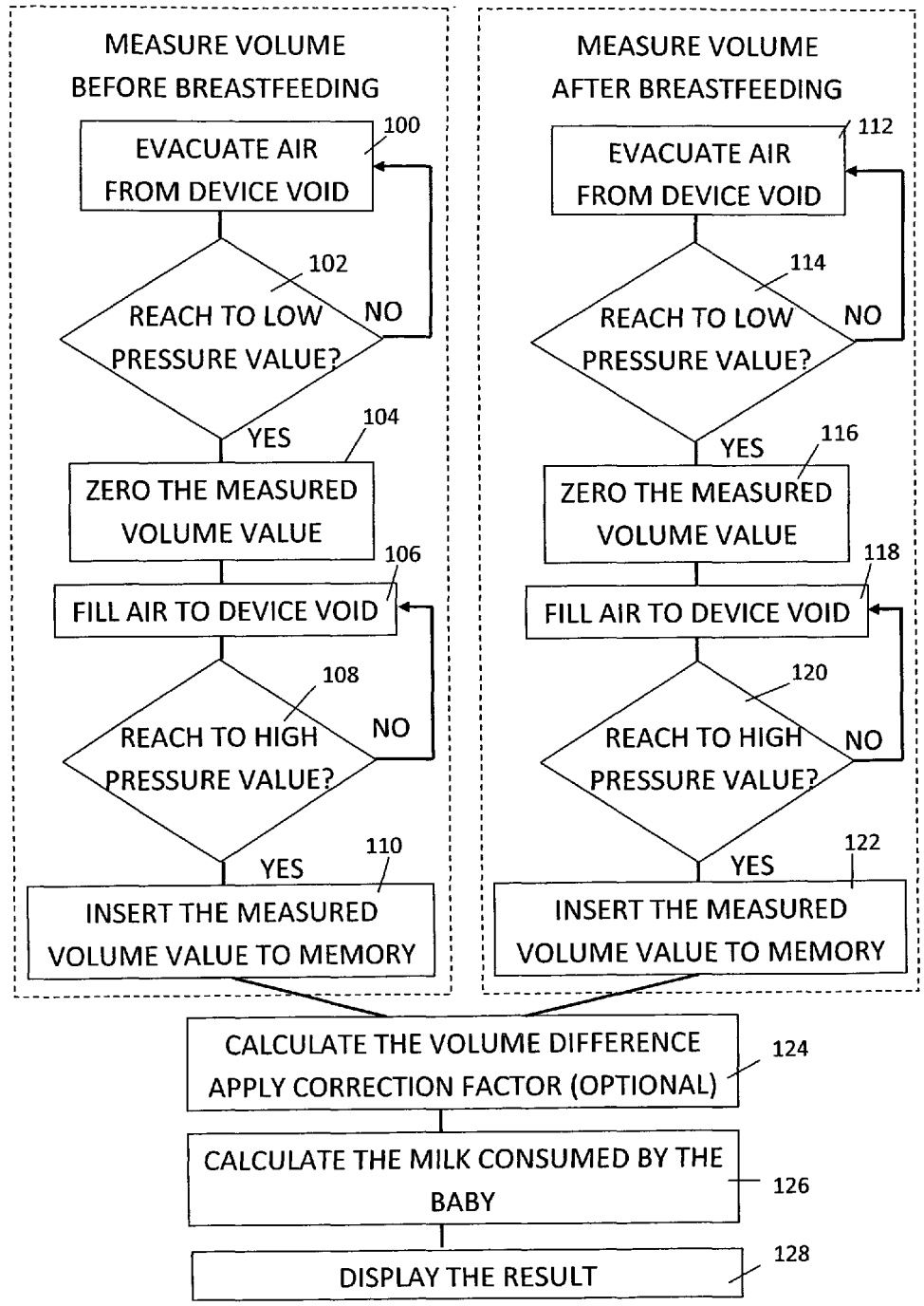
FIG. 12 is flow chart illustrating the method of measuring a quantity of breast milk, according to the present invention.

The method of measuring the quantity of breast milk suckled by a baby, according to the present invention, includes two main steps—determining a change in volume of a breast during breastfeeding (from before to after), preferably indirectly, so as not to interfere with the breastfeeding itself, and calculating the quantity of milk consumed as a function of the change in breast volume. One possible implementation of the invention will now be described with reference to FIG. 12. In this implementation, the change in volume is determined by indirectly by measuring the change in volume of the space of known volume (inside the cup) which is not filled by the breast. This is accomplished by indirectly measuring the breast volume before breastfeeding, indirectly measuring the breast volume after breastfeeding, and calculating the quantity of milk as a function of the change in breast volume. The volume of the breast before breastfeeding is calculated as follows. The breast interface unit is placed on the breast to be measured and may be held in place manually. In order to measure the air volume between the rigid envelope and the elastic sheet membrane in the breast interface, first the air space between these two elements should be evacuated (block 100). The pressure gauge is checked to determine whether the breast interface has been fully evacuated (i.e., has reached a pre-defined low pressure value) (block 102). When this pressure has been reached, this is the reference stage that zeros the device (block 104). In the second stage, the breast interface unit is placed to cover the breast. The user may now press a button indicating that the measurement before breastfeeding is to begin. In the third stage, the pumping mechanism fills the space in the breast interface with air or other fluid (block 106), until the membrane tightly fits the breast and wraps around it. When the pressure gage indicates that the void between the envelope and the elastic membrane is full of air (i.e., has reached a pre-determined high pressure value) (block 108), the volume is measured and the measured volume value is inserted to a memory (block 110). Thus, the total amount of air, at a given pressure, that was pumped into the space between the rigid envelope and the elastic membrane is measured and may be displayed.

It will be appreciated that utilizing a pressure gauge in this way normalizes the process in the device. In other words, the device reaches a repetitive "initiate process" reference point (pre-defined low pressure value) and reaches a repetitive "end process" reference point (pre-defined high pressure value).

This process is now repeated after breastfeeding, preferably being initiated by the user pressing a control button. Once again, the breast interface unit is placed to cover the breast, as nearly as possible in the same position as during the first measurement. The air space between the cup and the elastomer is evacuated (block 112). The pressure gauge is checked to determine whether the breast interface has been fully evacuated (i.e., has reached the pre-defined low pressure value) (block 114). Once this pressure has been reached, the membrane is tightly fitted to the envelope, and the reference stage that zeros the device has been reached (block 116). Now, as before, the pumping mechanism fills the space in the breast interface with air or other fluid (block 118), until the membrane tightly fits the breast and wraps around it. When the pressure gage indicates that the void between the envelope and the elastic membrane is full of air (i.e., has reached the pre-determined high pressure value) (block 120), the total amount of air, at this pressure, that was pumped into the void is measured and the measured volume value is inserted to a memory (block 122) and the difference between the two volume values is calculated (block 124).

It will be appreciated that, alternatively, at the end of the measurement before breastfeeding, the piston can be locked in place, for example, by providing inlet 82 with a one-way valve. Then, only the additional fluid introduced after breastfeeding need be measured to determine the change in breast volume.

Alternatively, the change in breast volume can be determined in any other suitable fashion that does not interfere with the breastfeeding itself, e.g., optically or finding system resonance in a pre-defined volume.

Finally, the milk consumed is determined according to the calculated difference (block 126) and may be displayed on the user interface (block 128). If required, one or more optional correction factors may be applied during this calculation. Such factors may depend on the duration of breastfeeding, the age of the baby and/or other factors known to affect the calculation of the quantity of milk suckled by the baby.

The apparatus according to the present invention measures the air volume using an accurate and unique method. The unique method can be better understood by the analogy to a syringe that fills air to a balloon and then evacuates it. Using this method, the system is fully controlled and sealed, since the same air inflates and deflates the balloon. An accurate measurement of the air amount, at a given pressure, in the balloon is reached by examining the syringe piston position on the syringe cylinder scale. A similar concept is implemented in the novel apparatus. The pumping unit evacuates and fills air by a sealed piston from/to a chamber, which is equivalent to the syringe cylinder. The sealed chamber shape might be cylinder, disc, ring, dome or other geometry, according to the design restrictions. The shape of the sealed piston, which functions as a partition and also pulls/pushes the air in the chamber, fits the sealed chamber shape. A scale and notches enable the user to know precisely the volume of air filled/evacuated to/from the space between the rigid envelope and the elastic membrane. According to alternative embodiments, the pumping unit can pump fluid directly into the space in the breast interface.

The system control of the device preferably is comprised of an electric gage that changes an electric property (like resistance or capacitance) as a function of the pumping mechanism operation.

The discrete position of the sealed piston in the sealed air chamber produces a characteristic electric value of voltage or electric current indicating the amount of air introduced into the space. It functions as a position encoder (i.e., rotary or linear, as required), as described above. Another electric principle that can be utilized for the encoder is a magnetic field and the Hall effect, for example. That enables the air volume, transferred between the device components at a given pressure, to be translated to an electric signal, input to the calculation unit. As described above, a pressure gage is used to normalize the process. The calculation unit gets electric inputs from the pressure gage to start the volume measuring process (low pressure value) and to stop the measuring process (pre-determined high pressure value). Alternatively, any other suitable stop mechanism can be employed to stop the operation of the pumping mechanism, for example, a proximity sensor to sense when the breast interface has conformed to the breast or to the shell.

An alternative mechanism for indicating the quantity of air introduced to the breast interface is a timer and flow-rate meter coupled to the pumping mechanism for measuring the flow-rate of the fluid that is introduced to the breast interface void. As shown in the figures, the fluid pumping mechanism is coupled to the driving chamber for introducing and removing fluid to the driving chamber, so as to drive the piston through the fluid chamber. The timer coupled to the pump provides an indication of the time during which the pumping mechanism was pumping and introducing (or removing) fluid. The quantity of fluid introduced can then be calculated by multiplying the measured flow-rate by the measured elapsed time while the pump was introducing fluid until the pumping mechanism was stopped.

Figure 13:
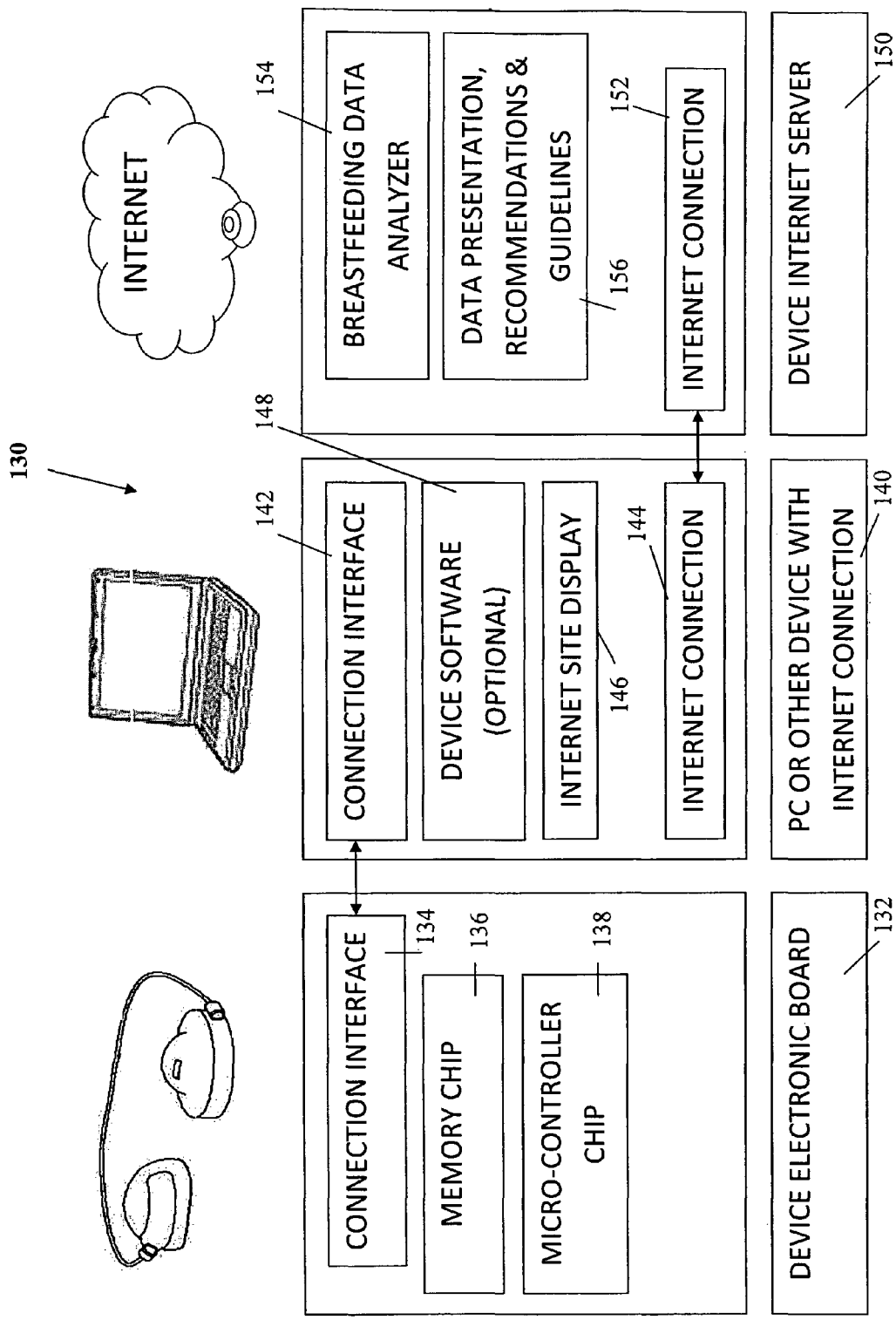
FIG. 13 is a block diagram illustration of a system for measuring a quantity of breast milk and analyzing breastfeeding data, according to one embodiment of the present invention.

FIG. 13 is a block diagram illustration of a system 130 for measuring a quantity of breast milk and analyzing breastfeeding data, according to one embodiment of the present invention. According to this embodiment, the electronic board 132 of the device for calculating the quantity of breast milk is coupled, by means of a connection interface 134 to the connection interface 142 of a computing device 140, which may be a laptop computer, a PDA, a PC, a smart cellular telephone, or any other suitable device having Internet connection capability. For this purpose, electronic board 132 further includes a memory chip 136 and a micro-controller chip 138, as known.

Alternatively, the data can be delivered to the computing device 140 by typing on the device's keyboard.

Computing device 140 includes an Internet connection module 144 and an Internet site display 146. Optional device software 148 may be provided, as desired. Most preferably, computing device 140 is coupled to a device Internet server 150 also having an Internet connection module 152. Device Internet server 150 preferably include a processing unit or breastfeeding data analyzer, for analyzing, over time, the breastfeeding data received from the device's electronic board 132. Server 150 may also include various data presentations, recommendations and guidelines 154 for breastfeeding mothers, which may be selected for display by the users.

An example of such an implementation will now be described. The device's electronic board includes a micro-controller, a memory chip, such as disk on chip, and a connection interface with a USB socket connector. The connection can be wireless, such as Bluetooth, in order to connect to a smart phone, for instance. During the breastfeeding milk measuring process, the micro-controller receives input data from the pressure gage and pumping mechanism encoder, in order to compute the amount of milk delivered to the baby, and writes it to the memory chip. The micro-controller takes input data from the memory chip, and delivers the result to the chip output that reaches the display component. The PC identifies the device identification when the USB wire connects the milk measuring device and the PC. A device software application provided in the PC approaches the appropriate memory address, uploads the data and saves it as a data file in the PC hard disk. Later on, the device application opens an Internet browser and uploads the data file to the device Internet server. Data analysis can then be performed on the server using all the data gathered from a specific user or from many users It will be appreciated that, in order to ensure accurate and consistent results, the breast interface must be positioned in substantially the same place and position each time a measurement is taken, particularly for each pair of before and after calculations. In order to assure the device is positioned in a repetitive way and presents accurate results, a learning process in the controller is one option. According to that approach, every measurement is taken at least two times. The measurement is approved as accurate when a repetitive result is received.

Figure 14:
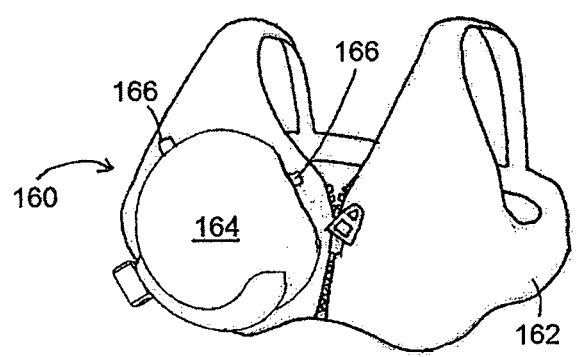
FIG. 14 is a schematic illustration of a positioning device option, according to one embodiment of the invention.

Another approach to reach to a repetitive positioning is using an additional accessory to enable repetitive usage. As an example, that kind of accessory can be designed similar to a brassiere design, that can be worn on the breast to position the devise in a substantially the same position each time it is worn. FIG. 14 is a schematic illustration of one positioning device 160, according to an embodiment of the invention. Positioning device 160 includes a support member 162, for example, shaped substantially like a camisole or brassiere, in which a breast interface 164 is mounted. When the support member 162 is worn on the woman's body, breast interface 164 will align substantially in the same position with the breast each time. If desired, connection elements 166 may be provided on support member 162 to which the breast interface 164 can be connected to ensure consistency. Connection elements 166 position and maintain breast interface 164 on support member 162 and, in turn, on the woman' breast. Preferably, the support member is designed to enable it to be used both for measuring milk consumed from the right breast and from the left breast.

Figure 15:
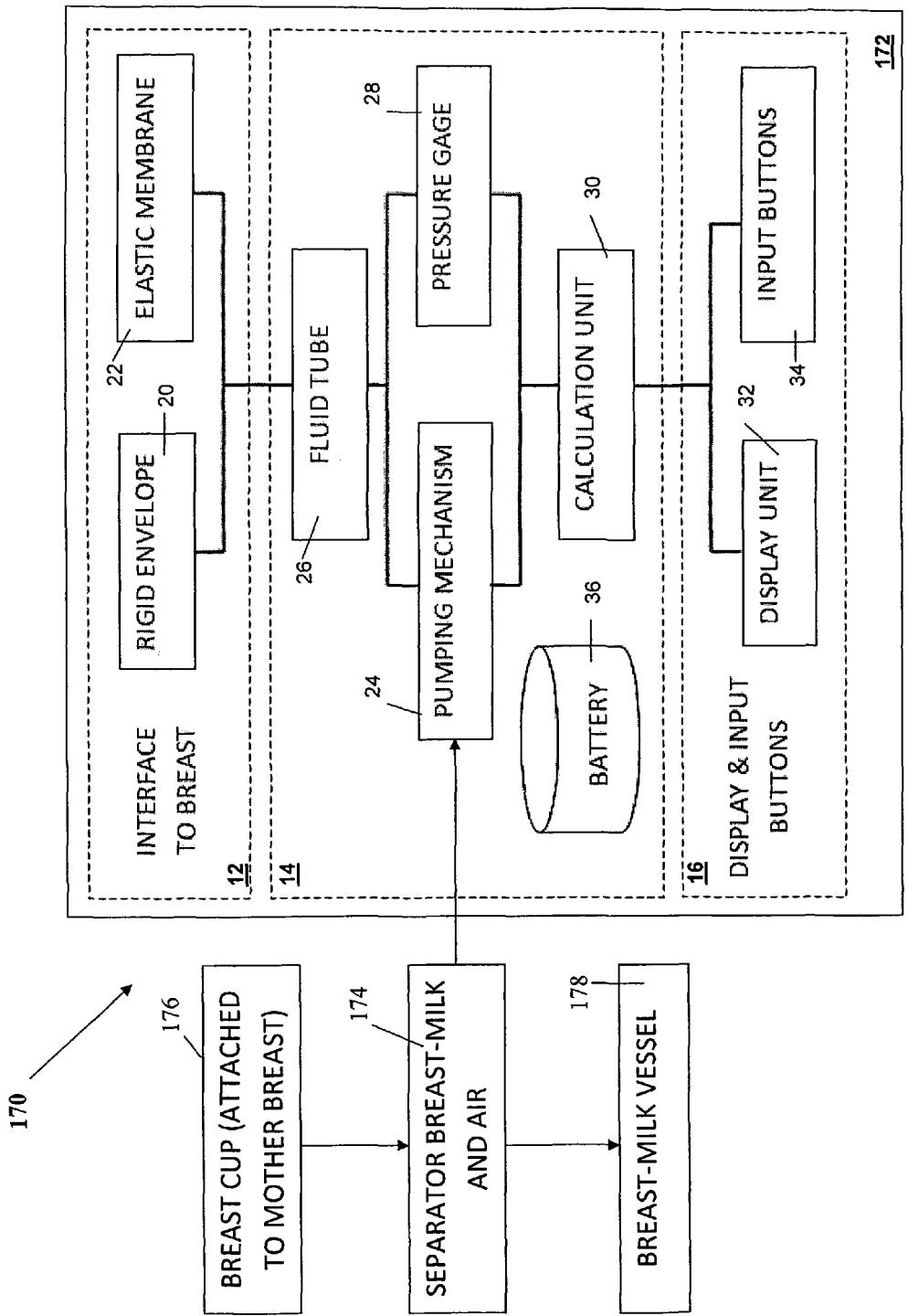
FIG. 15 is a block diagram illustration of a device for measuring breast milk with an incorporated breast pump, according to another embodiment of the invention.

When the pumping mechanism is implemented as an electric pump, additional design and additional components enable the device to function as a breastfeeding pump, as well. In such case, interfaces and adaptors should be supplemented, in order to fit the breast on one side and the baby's bottle on the other side. One possible embodiment is shown in FIG. 15, a block diagram illustration of a device 170 for measuring breast milk with an incorporated breast pump, according to another embodiment of the invention. Device 170 includes a device 172 for measuring a quantity of breast milk according to any embodiment of the invention, here illustrated as that in FIG. 1. Like elements have like reference numerals. Device 172 includes a pumping mechanism 24 which, in this embodiment, also serves as the pump for expressing breast milk from the breast. For this purpose, pumping mechanism 24 can also be coupled to a breast milk/air separator 174 coupled to a breast pump cup or horn 176. Breast pump cup 176 is designed to be held against a woman's breast, as in conventional breast pumps. A vessel 178 for holding the extracted breast milk may also be coupled to breast milk/air separator 174, if desired. In this way, a single device can be utilized by a mother, merely by exchanging the cup, to measure the amount of breast milk sucked or expressed from the breast, or to extract breast milk for later feeding, or both. It will be appreciated that the relevant components of the breast pump portion (breast pump cup, separator, vessel and device interfaces) should be compatible with delivery of both air and liquid.

The device for measuring a quantity of breast milk according to the invention may be manual, automated or semi-automated. The pumping mechanism can be manual or electrical. The process of moving the sealed piston in the sealed chamber can be implemented with a manual pump, with an electric pump, with an electric pull/push mechanism or manually, for example with a lever. In all cases, the volume of air is filled from a sealed chamber to the space between the rigid envelope and the elastic membrane.

Figure 16:
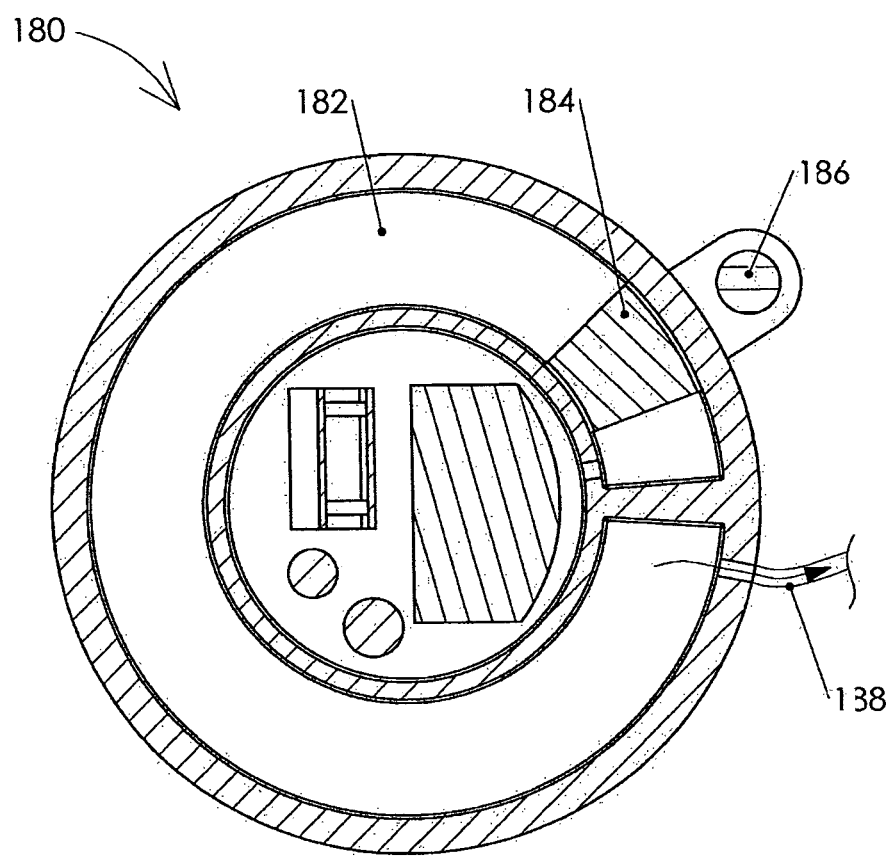
FIG. 16 is a schematic illustration of a device for measuring a quantity of breast milk, constructed and operative in accordance with a further embodiment of the invention.

One example of a manual device for measuring the quantity of breast milk is shown in FIG. 16. Device 180 includes an annular fluid chamber 182 with a piston 184 sealingly mounted therein. A manual position lever actuator 186 is coupled to piston 184 for moving piston 184 through fluid chamber 182, thereby forcing fluid out through an outlet 188 to a tube (not shown) connected to the breast interface. The amount of fluid moved from the fluid chamber to the breast interface can be determined as described above, i.e., using a position encoder to record the position of the piston, or using a flow meter in outlet 188.

It will be appreciated that the present invention permits calculation of the quantity of breast milk suckled by a baby by indirect measurement of the change in volume of the mother's breast, without interfering with the breastfeeding process, itself. The volume change is measured without the need to measuring the actual volume of the breast. The devices according to the invention are user friendly, simple to use and return rapid and accurate results, all at relatively low cost.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

The invention claimed is:

1. A device for measuring an amount of breast milk suckled during a breastfeeding session, the device comprising:
    a mechanism for determining a change in volume of a breast from before the breastfeeding session to after the breastfeeding session, said mechanism including a mechanism for measuring a quantity of fluid introduced into a space of defined volume around the breast, first before the breastfeeding session and again after the breastfeeding session, and providing an indication thereof; and
    a calculation unit for calculating, from said measured quantities of fluid, a change in volume of the breast and a quantity of breast milk suckled during the breastfeeding session, wherein said calculation unit is coupled to said mechanism for measuring, receives the indications of said measured quantities of fluid in the space around the breast and calculates said quantity of suckled milk from a change in said measured quantities of fluid measured before and after the breastfeeding session;
    wherein said calculation unit comprises an electronic board including:
    a memory chip; and
    a micro-controller chip.

2. The device according to claim 1, wherein said mechanism for determining a change comprises:
    a fluid chamber coupled to said space forming a closed system;
    a piston sealingly mounted in said chamber for slideable movement therethrough;
    and a device selected from the group including a manual pump, an electric pump, an electric pull/push mechanism, a manual lever, for moving said sealed piston in said chamber.

3. The device according to claim 1, further including means for performing a self-calibration process by means of:
    measuring the said space before every breastfeeding; and
    evacuating the air from the said space before introducing air and measuring the volume of the said space.

4. The device according to claim 1, wherein said electronic board further includes a connection interface for connection to a computing device coupled to a device Internet server having a processing unit for analyzing breastfeeding milk quantity data.

5. The device according to claim 1, wherein said mechanism for determining change includes:
    a breast interface for placing on a breast, said breast interface defining an expandable space;
    a fluid pump for removing fluid from and introducing fluid into said space; and
    a mechanism for indicating a quantity of fluid pumped into or removed from said space comprising a timer and flow-rate meter coupled to said pumping mechanism for measuring a flow-rate of fluid that is introduced to the space of defined volume around the breast and providing an indication of time during which said pumping mechanism was pumping and said measured flow-rate to said calculation unit for calculating change of volume.

6. The device according to claim 1, wherein said mechanism for determining change includes:
    a breast interface for placing on a breast, said breast interface defining an internal space;
    a fluid pump coupled to said breast interface for removing fluid from and introducing fluid into said space;
    a control mechanism coupled to said fluid pump for indicating to said pump to start or stop pumping; and
    a mechanism for indicating a quantity of fluid pumped into said space until said pump was stopped.

7. The device according to claim 6, wherein said breast interface includes a rigid envelope and an elastic membrane affixed to said rigid envelope, said space being defined between said rigid envelope and said elastic membrane, wherein said breast interface is shaped to fit a breast geometry.

8. The device according to claim 1, wherein said mechanism for determining change includes:
    a breast interface for placing on a breast, said breast interface defining an expandable space;
    a fluid pump for removing fluid from and introducing fluid into said space;
    a fluid pressure gauge coupled to said space and to said fluid pump for measuring fluid pressure in said space for indicating an initial point and an end point for introduction of fluid to said space by said fluid pump; and
    a device for providing an indication of a total volume of fluid introduced to said space.

9. The device according to claim 8, wherein said breast interface includes a rigid envelope and an elastic membrane affixed to said rigid envelope, said space being defined between said rigid envelope and said elastic membrane, wherein said breast interface is shaped to fit a breast geometry.

10. A device for measuring an amount of breast milk suckled during a breastfeeding session, the device comprising:
    a mechanism for determining a change in volume of a breast from before the breastfeeding session to after the breastfeeding session, said mechanism including a mechanism for measuring a quantity of fluid introduced into a space of defined volume around the breast, first before the breastfeeding session and again after the breastfeeding session, and providing an indication thereof; and
    a calculation unit for calculating, from said change in volume, a quantity of breast milk suckled during the breastfeeding session, wherein said calculation unit is coupled to said mechanism for measuring and receives the indications of measured quantities of fluid in the space around the breast and calculates said quantity of suckled milk from a change in said measured quantities of fluid measured before and after the breastfeeding session;
    wherein said mechanism for determining a change comprises:
    a fluid chamber coupled to said space forming a closed system;
    a piston sealingly mounted in said chamber for slideable movement therethrough;
    a fluid pumping mechanism coupled to a driving chamber, the fluid pumping mechanism introducing and removing fluid to said driving chamber for driving said piston through said fluid chamber; and a mechanism for indicating a quantity of fluid pumped into or removed from said space selected from the group consisting of:

a position encoder for indicating a position of said piston; and a timer and flow-rate meter coupled to said pumping mechanism for measuring a flow-rate of fluid that is introduced to the space of defined volume around the breast and providing an indication of time during which said pumping mechanism was pumping and said measured flow-rate to said calculation unit for calculating change of volume.

11. A device for measuring an amount of breast milk suckled during a breastfeeding session, the device comprising:

a mechanism for determining a change in volume of a breast from before the breastfeeding session to after the breastfeeding session, said mechanism including a mechanism for measuring a quantity of fluid introduced into a space of defined volume around the breast, first before the breastfeeding session and again after the breastfeeding session, and providing an indication thereof; and a calculation unit for calculating, from said change in volume, a quantity of breast milk suckled during the breastfeeding session, wherein said calculation unit is coupled to said mechanism for measuring and receives the indications of measured quantities of fluid in the space around the breast and calculates said quantity of suckled milk from a change in said measured quantities of fluid measured before and after the breastfeeding session;

wherein said mechanism for determining a change includes:

a breast interface for placing on a breast, said breast interface defining an internal space;

a fluid pump coupled to said breast interface for removing fluid from and introducing fluid into said space;

a control mechanism coupled to said fluid pump for indicating to said pump to start or stop pumping; and a mechanism for indicating a quantity of fluid pumped into said space until said pump was stopped;

said device further comprising an incorporated breast pump including a breast pump cup and a breast milk/air separator coupled to said pumping mechanism.

* * * * *